US007674596B2

(12) United States Patent
Jeong et al.

(10) Patent No.: US 7,674,596 B2
(45) Date of Patent: Mar. 9, 2010

(54) TRANSFECTED CELL LINE AND A METHOD USING THE SAME FOR THE HIGH THROUGHPUT SCREENING FOR INHIBITORS OF THE T-TYPE CALCIUM CHANNEL ALPHA-1H

(75) Inventors: Seong-Woo Jeong, Gangwon-do (KR); Jung-Ha Lee, Gyeonggi-do (KR); Byong-Gon Park, Gangwon-do (KR); Edward Perez-Reyes, Charlottesville, VA (US); Dong Jin Kim, Seoul (KR); Hee Sup Shin, Gyeonggi-do (KR); Taehyun Kim, Seoul (KR); Hyewhon Rhim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 837 days.

(21) Appl. No.: 11/162,487

(22) Filed: Sep. 12, 2005

(65) Prior Publication Data
US 2006/0194253 A1  Aug. 31, 2006

(30) Foreign Application Priority Data
Feb. 26, 2005  (KR) .................. 10-2005-0016221

(51) Int. Cl.
*C12N 5/10* (2006.01)
*G01N 33/53* (2006.01)
(52) U.S. Cl. .............. 435/7.2; 435/325; 435/375
(58) Field of Classification Search .................. None
See application file for complete search history.

(56) References Cited

U.S. PATENT DOCUMENTS

| 6,576,434 | B1 | 6/2003 | Holroyd et al. |
| 6,899,800 | B2 | 5/2005 | Osipchuk et al. |
| 6,984,521 | B2 * | 1/2006 | Han et al. .................. 435/366 |
| 2004/0121381 | A1 | 6/2004 | Normant et al. |
| 2005/0130298 | A1 * | 6/2005 | Han et al. .................. 435/325 |

OTHER PUBLICATIONS

Taehyun Kim et al., "The biochemical activation of T-type Ca2+ channels in HEK293 cells stably expressing α1G and Kir2.1 subunits" BBRC, Sep. 2004.
Yue-Qun Wang et al., "Functional Analysis of the Human T-type Calcium Channel α1H Subunit Gene in Cellular Proliferation."
Park et al., "Development and Evaluation of Stable Cell Lines for Fluorescent Dye-Based T-Type Calcium Channel Assay Essential to High-Throughput Screening of Drugs," Program No. 735.12 Society for Neuroscience, 2004. Online.
Brueggemann et al., "Ion Channel Drug Discovery and Research: The Automated Nano-Patch-Clamp© Technology", Current Drug Discovery Technologies, 1: 91-96 (2004).
Bernheim, L., and Bader, C., "Human Myoblast Differentiation: Ca2+ Channels are Activated by K+ Channels," News Physiology Science, 17: 22-26 (Feb. 2002).
Fertig et al., "Whole Cell Patch Clamp Recording Performed on a Planar Glass Chip," Biophysical Journal, 82: 3056-3062 (Jun. 2002).
Klemic et al., "Micromolded PDMS planar electrode allows patch clamp electrical recordings from cells," Biosensors and Bioelectronics, 17: 597-604 (2002).
Guo, Weinong, et al., "Cell Cycle-related Changes in Voltage-gated Ca2+ Currents in Cultured Newborn Rat Ventricular Myocytes," J Mol Cell Cardiol (1998) 30:1095-1103.
Cribbs, et al., "Cloning and Characterization of α1H From Human Heart, a Member of the T-Type $Ca^2$ + Channel Gene Family," Circ. Res. (1998) 83:103-109.
Huguenard, J.R., "Low-Threshold Calcium Currents in Central Nervous System Neurons," Annu. Rev. Physiol. (1996) 58:329-48.
Perez-Reyes, et al., "Molecular characterization of a neuronal low-voltage-activated T-type calcium channel," Nature (1998) 391:896-900.

* cited by examiner

*Primary Examiner*—Michael Pak
(74) *Attorney, Agent, or Firm*—Joseph Hyosuk Kim; JHK Law

(57) ABSTRACT

The present invention relates to a cell line in which a potassium channel is introduced. More specifically, it is a cell line capable of activating the T-type α1H calcium channel by depolarization wherein a vector encoding a potassium channel is introduced. Since the cell line of the present invention is available for a high throughput screening of candidate T-type α1H calcium channel inhibitors, it may accelerate the development of therapeutic agents for diseases related to T-type α1H calcium channels.

7 Claims, 8 Drawing Sheets

FIG. 1 forward primer site

```
   1   atgggcagtgtgcgaaccaaccgctacagcatcgtctcttcagaagaagacggtatgaag
  61   ttggccaccatggcagttgcaaatggctttgggaacgggaagagtaaagtccacacccga
 121   caacagtgcaggagccgctttgtgaagaaagatggccactgtaatgttcagttcatcaat
 181   gtgggtgagaaggggcaacggtacctcgcagacatcttcaccacgtgtgtggacattcgc
 241   tggcggtggatgctggttatcttctgcctggctttcgtcctgtcatggctgttttttggc
 301   tgtgtgttttggttgatagctctgctccatggggacctggatgcatccaaagagggcaaa
 361   gcttgtgtgtccgaggtcaacagcttcacggctgccttcctcttctccattgagacccag
 421   acaaccataggctatggtttcagatgtgtcacggatgaatgcccaattgctgttttcatg
 481   gtggtgttccagtcaatcgtgggctgcatcatcgatgctttcatcattggcgcagtcatg
 541   gccaagatggcaaagccaagaagagaaacgagactcttgtcttcagtcacaatgccgtg
 601   attgccatgagagacggcaagctgtgtttgatgtggcgagtgggcaatcttcggaaaagc
 661   cacttggtggaagctcatgttcgagcacagctcctcaaatccagaattacttctgaaggg
 721   gagtatatccctctggatcaaatagacatcaatgttgggtttgacagtggaatcgatcgt
 781   atatttctggtgtccccaatcactatagtccatgaaatagatgaagacagtcctttatat
 841   gatttgagtaaacaggacattgacaacgcagactttgaaatcgtggtcatactggaaggc
 901   atggtggaagccactgccatgacgacacagtgccgtagctcttatctagcaaatgaaatc
 961   ctgtggggccaccgctatgagcctgtgctctttgaagagaagcactactacaaagtggac
1021   tattccaggttccacaaaacttacgaagtcccaacactcccctttgtagtgccagagac
1081   ttagcagaaaagaaatatatcctctcaaatgcaaattcatttgctatgaaaatgaagtt
1141   gccctcacaagcaaagaggaagacgacagtgaaaatggagttccagaaagcactagtacg
1201   gacacgcccctgacatagaccttcacaaccaggcaagtgtacctctagagcccaggccc
1261   ttacggcgagagtcggagatatgagactgattccttctctggaatagttactttacaaca
1321   cggtct
``` reverse primer site (SEQ ID NO:1)

FIG. 2

```
  1  Met Gly Ser Val Arg Thr Asn Arg Tyr Ser Ile Val Ser Ser Glu Glu Asp Gly Met Lys
 21  Leu Ala Thr Met Ala Val Ala Asn Gly Phe Gly Asn Gly Lys Ser Lys Val His Thr Arg
 31  Gln Gln Cys Arg Ser Arg Phe Val Lys Lys Asp Gly His Cys Asn Val Gln Phe Ile Asn
 41  Val Gly Glu Lys Gly Gln Arg Tyr Leu Ala Asp Ile Phe Thr Thr Cys Val Asp Ile Arg
 51  Trp Arg Trp Met Leu Val Ile Phe Cys Leu Ala Phe Val Leu Ser Trp Leu Phe Phe Gly
 61  Cys Val Phe Trp Leu Ile Ala Leu Leu His Gly Asp Leu Asp Ala Ser Lys Glu Gly Lys
 71  Ala Cys Val Ser Glu Val Asn Ser Phe Thr Ala Ala Phe Leu Phe Ser Ile Glu Thr Gln
 81  Thr Thr Ile Gly Tyr Gly Phe Arg Cys Val Thr Asp Glu Cys Pro Ile Ala Val Phe Met
 91  Val Val Phe Gln Ser Ile Val Gly Cys Ile Ile Asp Ala Phe Ile Ile Gly Ala Val Met
101  Ala Lys Met Ala Lys Pro Lys Lys Arg Asn Glu Thr Leu Val Phe Ser His Asn Ala Val
111  Ile Ala Met Arg Asp Gly Lys Leu Cys Leu Met Trp Arg Val Gly Asn Leu Arg Lys Ser
121  His Leu Val Glu Ala His Val Arg Ala Gln Leu Leu Lys Ser Arg Ile Thr Ser Glu Gly
131  Glu Tyr Ile Pro Leu Asp Gln Ile Asp Ile Asn Val Gly Phe Asp Ser Gly Ile Asp Arg
141  Ile Phe Leu Val Ser Pro Ile Thr Ile Val His Glu Ile Asp Glu Asp Ser Pro Leu Tyr
151  Asp Leu Ser Lys Gln Asp Ile Asp Asn Ala Asp Phe Glu Ile Val Val Ile Leu Glu Gly
161  Met Val Glu Ala Thr Ala Met Thr Thr Gln Cys Arg Ser Ser Tyr Leu Ala Asn Glu Ile
171  Leu Trp Gly His Arg Tyr Glu Pro Val Leu Phe Glu Glu Lys His Tyr Tyr Lys Val Asp
181  Tyr Ser Arg Phe His Lys Thr Tyr Glu Val Pro Asn Thr Pro Leu Cys Ser Ala Arg Asp
191  Leu Ala Glu Lys Lys Tyr Ile Leu Ser Asn Ala Asn Ser Phe Cys Tyr Glu Asn Glu Val
201  Ala Leu Thr Ser Lys Glu Glu Asp Asp Ser Glu Asn Gly Val Pro Glu Ser Thr Ser Thr
211  Asp Thr Pro Pro Asp Ile Asp Leu His Asn Gln Ala Ser Val Pro Leu Glu Pro Arg Pro
221  Leu Arg Arg Glu Ser Glu Ile ***
```

(SEQ ID NO:2)

FIG. 8
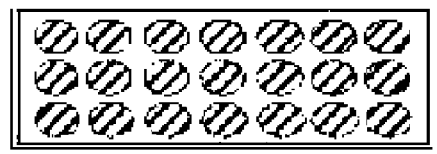
A
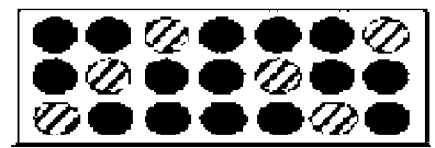
B

TRANSFECTED CELL LINE AND A METHOD USING THE SAME FOR THE HIGH THROUGHPUT SCREENING FOR INHIBITORS OF THE T-TYPE CALCIUM CHANNEL ALPHA-1H

BACKGROUND OF THE INVENTION (a) Field of the Invention

The present invention relates to a cell line in which a potassium channel is exogenously expressed; more specifically, it relates to a transfected cell line prepared by introducing a vector containing a gene encoding a potassium channel into a cell line that stably expresses T-type α1H calcium channels.

On the other hand, the present invention relates to a high throughput screening method for inhibitors of T-type α1H calcium channels using the above cell line.

(b) Description of the Related Art

The T-type channel is a member of voltage-dependent $Ca^{2+}$ channels activated by low voltage. Three subtypes (α1G, α1H and α1I) of the gene encoding the T-type channel have been found so far (Perez-Reyes et al., *Nature*, 391:896-900, 1998; Cribbs et al., *Cir. Res.*, 83:103-109, 1998; Lee et al., *J. Neurosci.*, 19:1912-1921, 1999). When the subtypes of T-type channel are expressed in heterologous expression systems, e.g., Xenopus oocytes and HEK293 cell lines, they show such biophysical characteristics as (a) activation of the channel at low voltage around −60 mV, (b) rapid activation or non-activation of the channel, (c) a remarkably slow deactivation and (d) small conductance.

According to the prior arts, the T-type α1H channel plays an important role in regulating neuronal excitability in the central nervous system (Huguenard et al., *Annu. Rev. Physiol.*, 58:329-334, 1996). In addition, T-type α1H channel regulates a variety of biological functions such as the heartbeat (Hagiwara et al., *J. Physiol.*, 395:233-253), hormone secretion (Cohen et al., *Proc. Natl. Acad. Sci. USA*, 85:2412-2416, 1988; Enyeart et al., *Mol. Endocrinol.*, 7:1031-1040, 1993), contraction of smooth muscle (Akaike et al., *J. Physiol.*, 416:141-160, 1989), reproduction (Arnoult et al., *Proc. Natl. Acad. Sci. USA*, 93:13004-13009, 1996) and cell growth and differentiation (Berridge, *Neuron*, 21:13-26, 1998; Guo et al., *J. Mol. Cell Cardiol.*, 30:1095-1103, 1998; Kono et al., *J. Cell Biol.*, 132:915-923, 1996), etc.

When the T-type α1H channel is over-expressed by genetic or other reasons, diseases like absence epilepsy (Huguenard et al., *J. Neurosci.*, 14:5485-5502, 1994; Tsakiridou et al., *J. Neurosci.*, 15:3110-3117, 1995; Kim et al., *Neuron*, 31:35-45, 2001), heart disease (ex, ventricular hypertrophy and hypertension) (Nuss et al., *Cir. Res.*, 73:777-782, 1993; Martinez et al., *J. Mol. Cell Cardiol.*, 31:1617-1625, 1999), neuropathic pain (Dogrul et al., *Pain*, 105:159-168, 2003) and prostatic cancer (Mariot et al., *J. Biol. Chem.*, 277:10824-10833) might be developed.

Therefore, T-type α1H channel has been a major target of studies on new drug development, world-wide. The importance of the study on the mechanism regulating the characteristics of the T-type α1H channel (biophysical and pharmacological properties, gene expression and transport regulation, signal transduction, etc), in physiological and pathophysiological conditions, is in no doubt because such studies enable the discovery of candidates for a new drug.

In order to develop a new drug inhibiting the T-type α1H channel, it is important that organic chemists explore the lead chemicals and design and synthesize their related compounds. For a successful new drug development, a high throughput screening (HTS) system, which investigates whether or not the synthesized materials can inhibit the T-type α1H channel rapidly and effectively, has to be established first.

Whether the synthesized materials are T-type α1H channel inhibitors or not is confirmed by measuring the calcium current with the conventional electrophysiological (namely, patch-clamp) method. This method has an advantage of providing the most accurate information on ion channels but has a problem of limitation in data points (the number of test compounds) per unit time, so the method might be inadequate for detecting lots of materials in a short time.

Recently, a patch-clamp HTS system enabling the electrical measurement of the activity of a T-type α1H channel has been developed by Axon Instruments (USA). This system may be a possible choice for researchers in overcoming the above problem in the new drug development related to the T-type α1H channel. Still a question remains to be answered whether such system can satisfactorily process the sophisticated and complex sequence of the patch-clamp method.

An alternative to the electrophysiological HTS is a detection method for searching T-type α1H channel inhibitors by measuring fluorescence. Instead of measuring the calcium current, this method evaluates the activity of calcium channel indirectly by measuring the fluorescence intensity which increases in proportion to the calcium influx through T-type α1H channels using calcium-binding fluorescent dyes such as fura. However, this method has the disadvantage of not being able to regulate the opening and closing of T-type α1H channels, unlike such voltage clamp methods as the patch clamp.

Well aware of the above mentioned problems in conventional high throughput screening approaches, the inventors thus developed a cell line and a HTS method based on it. In the cell line, a potassium channel was introduced to HEK293 cells, which stably expresses T-type α1H channels. The cells activate T-type α1H channels when a high concentration of potassium chloride is added to the extracellular medium without any electrical stimulus through maintaining a high resting potential in them. From the experiments, it was confirmed that T-type α1H channels are activated by depolarization upon the addition of a high concentration of KCl outside the cell. We were able to detect the resultant changes in the $Ca^{2+}$ influx with a high signal-to-noise fluorescence ratio. The present inventors thus completed this invention by confirming that the cell line of the present invention is the optimal cell line for the high throughput screening and broad-spectrum studies of T-type α1H calcium channel inhibitors.

SUMMARY OF THE INVENTION

A cell line with a novel calcium signaling characteristic and a method based on the said cell line, for a high throughput screening of candidate inhibitors of T-type α1H channels are provided in this application. The cell line is prepared by transfecting a cell line that stably expresses T-type α1H channels with a vector containing a gene encoding a potassium channel.

Such a cell line is capable of activating T-type α1H channels by depolarization when a high concentration of KCl is added, since the inserted gene encoding a potassium channel effects a high resting membrane potential in the cells.

Since the said cell line is capable of giving a strong calcium florescence signal without electrical stimuli, it suitable for a high throughput screening of the inhibitors of the T-type α1H channel. Also it is a useful construct for broad-spectrum studies on T-type α1H channels.

BRIEF DESCRIPTION OF THE DRAWINGS

FIG. 1 is a schematic diagram showing the nucleotide sequence of human potassium channel Kir2.1.

FIG. 2 is a schematic diagram showing the amino acid sequence of the human potassium channel Kir2.1.

FIG. 4A is a graph showing the record of the T-type current activated by a ramp stimulus and inwardly rectified potassium (IRK) current in the cell line HEK293-TChH-IRK2.1 of the present invention; FIG. 4B is a graph showing the barium-sensitive IRK current recorded upon a test stimulus; FIG. 4C is a graph that shows the result confirming the formation of a resting membrane potential in the same cell; FIG. 4D is a graph showing the calcium action potential of a cell with a recorded resting membrane potential during depolarization induced by barium, a Kir2.1 inhibitor.

FIGS. 8A and 8B are schematic diagrams showing a possible selection scheme in a high throughput screening using the cell line of this invention. The cells seeded on the wells of a 96-well plate is incubated with a test drug and a fluorescent dye (8A). Upon adding a high concentration of KCl, the cells with strong or no fluorescence (8B) can be selected.

DETAILED DESCRIPTION OF THE PREFERRED EMBODIMENTS

Figure 3:
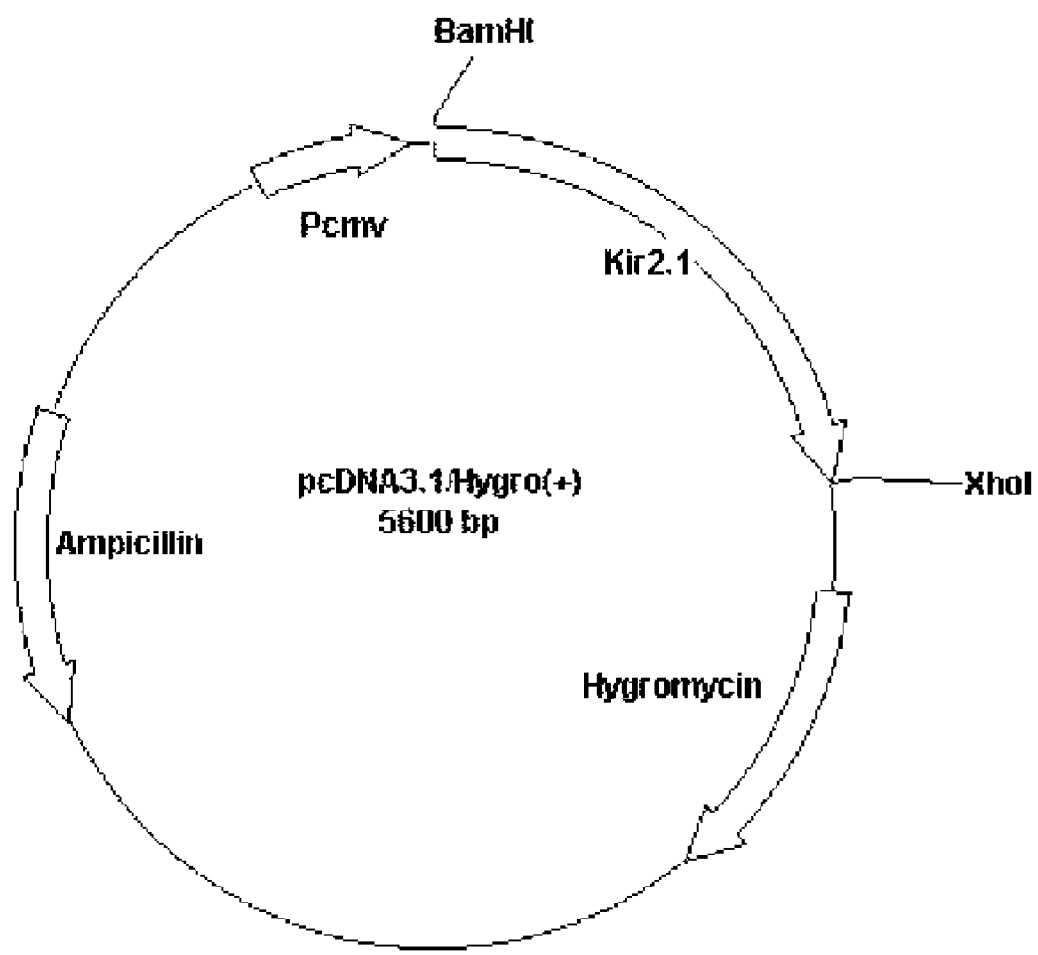
FIG. 3 is a schematic diagram showing the cleavage map of hKir2.1-pcDNA3.1(+) vector in which the human potassium channel Kir2.1 is sub-cloned.

To achieve the objects mentioned above, the present invention provides a cell line prepared by inserting a vector containing the gene encoding a potassium channel in cells expressing T-type α1H calcium channel.

The present invention also provides a screening method for T-type α1H calcium channel inhibitors by using the above cell line.

Hereinafter, the present invention is described in detail.

The present invention provides a cell line prepared by inserting a vector containing a gene coding potassium channel in cells expressing T-type α1H calcium channel.

There is a technical problem in establishing an HTS system to detect calcium fluorescence signals. That is, the resting membrane potential of the HEK293 cell line where T-type α1H calcium channel is stably expressed is so low that most T-type α1H channels are totally inactivated (Perez-Reyes et al., *Nature*, 391:896-900, 1998; Cribbs et al., *Cir. Res.*, 83:103-109, 1998; Lee et al., *J. Neurosci.*, 19:1912-1921, 1999). Thus, sufficient calcium signals cannot be obtained by the depolarization of cell membrane with a high concentration of KCl.

In order to find the characteristics of the T-type α1H channel, heterologous expression systems such as HEK293 cells have been hired to express the channel transiently or stably therein. However, the uses of the HEK293 cell line are limited in that the characteristics of T-type α1H channel (ex, biophysical and pharmacological properties, gene expression and transport regulation, phosphorylation level, signal transduction, etc) observed in excitable tissues with high resting membrane potentials may turn out to be very different from those in HEK239 cells. Thus, it is an object of the present invention to provide a cell line capable of calcium signaling via the activation of the T-type α1H channel induced upon adding a high concentration of KCl. Such a cell line can be prepared by loading a high resting membrane potential to HEK293 cells stably expressing the T-type α1H channel.

In the present invention, a gene represented by SEQ ID NO:1, coding the human potassium channel Kir2.1 (hKir2.1-Genebank accession No.: AF153820), which plays an important role in the formation of resting membrane potential, was cloned and HEK293 cells (Dr. Edward Perez-Reyes, Department of Pharmacology, University of Virginia) expressing the human T-type α1H calcium channel (hCav3.2-Genebank accession No.: AF051946) stably were transfected with the gene above. Then transformed colonies were screened using antibiotic selection. Patch-clamp and intracellular calcium content measurements were performed with the selected clones, and then the best transformed cell line was chosen. As a result, a cell line was established that has the characteristics of a high resting membrane potential and gives a strong calcium signal by the activation of T-type α1H channels e when a high concentration of KCl or barium is added. It was named HEK293-TChH-IRK2.1. The HEK293-TChH-IRK2.1 cell line of the present invention was deposited at the Korean Collection for Type Cultures (KCTC) of the Korea Research Institute of Bioscience and Biotechnology (KRIBB) on Feb. 22, 2005 (Accession No: KCTC 10780BP).

It was investigated whether the non-electrophysiological fluorescence calcium detection method using the cell line of the present invention could (1) obtain a strong calcium signal, and (2) confirm the blocking of calcium signal by T-type α1H channel specific inhibitors.

While an artificial electric stimulus is given to activate T-type α1H channels in the patch clamp method, barium or KCl has to be supplied outside the cell for depolarization in the non-electrophysiological fluorescence detection since the cell itself has a sufficient resting membrane potential.

Figure 5:
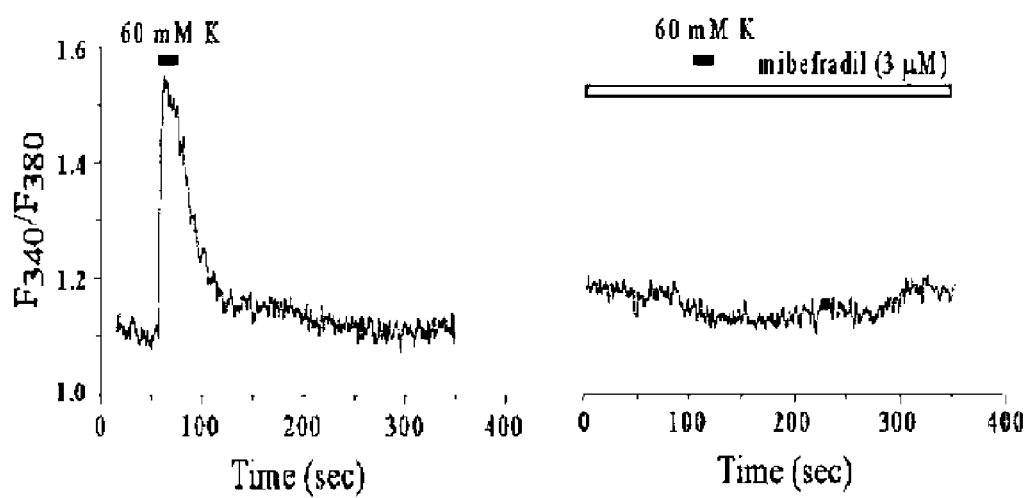
FIG. 5 is a set of graphs showing the results from the measurement of calcium fluorescence signals in the cell line HEK293-TChH-IRK2.1 of the present invention. The resultant changes in $F_{340}/F_{380}$ by the calcium influx during depolarization induced by adding a high concentration of KCl, after loading the fluorescent dye fura-2/AM in the cell line, was measured after a amplifying the signal with a photomultiplier (PM) tube

When a single cell of a clone (cells expressing T-type α1H channel and hKir2.1 stably), loaded with Fura-2/AM was depolarized by 60 mM KCl, the $F_{340}/F_{380}$ ratio was increased from 1.1 to 1.55, and the increase in the calcium influx through T-type α1H channels was completely blocked by a pre-treatment with mibefradil, a nonspecific T-type channel inhibitor (see FIG. 5). The $F_{340}/F_{380}$ ratio in a cell varied with the extracellular calcium content, which was 2 mM and 10 mM when the calcium content in the extracellular fluid was 0.18±0.06 (number of tests=6) and 0.59±0.07 (number of tests=6) respectively, suggesting that the $F_{340}/F_{380}$ ratio was increased in proportion to the calcium content in the extracellular fluid.

The cooled CCD imaging system which can simultaneously measure fluorescent images of calcium signals from various cells, provides an experimental environment and principles similar to those provided by the fluorescent imaging plate reader (FLIPLR) used in a high throughput screening of drugs. Thus, the present invention used this imaging system to confirm whether or not the cell line of the present invention was adequate for detecting T-type α1H channel inhibitors with high efficiency. In order to measure the fluorescent calcium image, fluo-3 was loaded into the cells. As a result, the intracellular calcium level was slightly increased (some cells turned red) even at a non-depolarized resting phase without loading KCl. We confirmed, however, that such increase in the calcium level was remarkably reduced (the number of red cells were significantly decreased) by a pretreatment with mibefradil, a non-specific T-type channel inhibitor.

Figure 6:
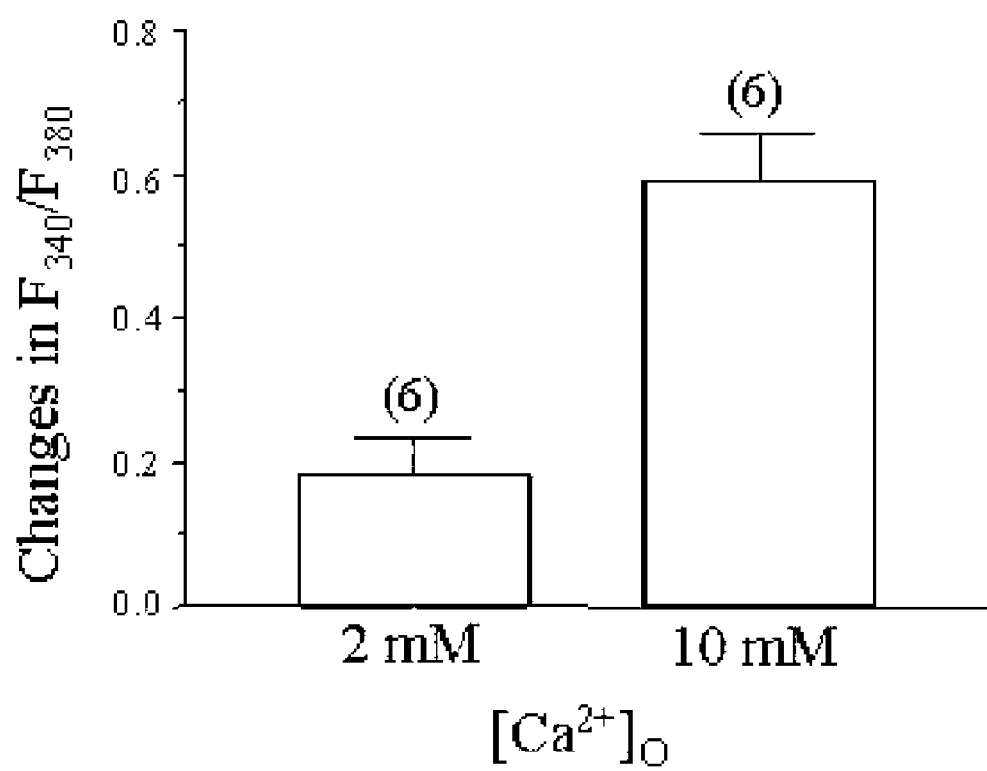
FIG. 6 is a graph showing changes in the $F_{340}/F_{380}$ ratio in proportion to the extracellular calcium level in the cell line HEK293-TChH-IRK2.1, indicating an increase of calcium signal therein.

When depolarization was induced in the cells by adding 60 mM KCl, the fluorescent image brightened very rapidly (see FIG. 6). The increase of intracellular calcium signal was completely inhibited by the pre-treatment with either mibefradil, a non-specific T-type channel inhibitor, or 100 mM $Ni^{2+}$ (see FIG. 7).

As explained above, depolarization was induced in the cell line of the present invention when a high concentration of KCl was added outside the cells, leading to the activation of the T-type α1H channel. We were able to monitor the influx of calcium ions by measuring ratio the fluorescence signals with a high signal-to-noise ratio. As a result, the cell line of the present invention was confirmed to be the optimal cell line for detecting T-type α1H calcium channel inhibitors and the broad-spectrum studies on their characteristics.

The present invention also provides a screening method for T-type α1H calcium channel inhibitors using the above cell line.

When the T-type α1H calcium channel is over-expressed in tissues owing to genetic or other reasons, such diseases as absence epilepsy, heart disease (ex, ventricular hypertrophy and hypertension), neuropathic pain or prostatic cancer might be developed. Therefore, the T-type α1H channel has been a major target of studies on new drug development world-wide, and a T-type calcium channel inhibitor can be a promising drug candidate for related diseases.

The screening method of the present invention preferably comprises the following steps:
  i) Loading a fluorescent dye into the cells;
  ii) Adding a test drug into the cells of the above step i);
  iii) Depolarizing the cells of the above step ii); and
  iv) Measuring the fluorescence intensity in the cells of the above step iii).

By monitoring the cells showing no fluorescence changes or weak fluorescence in step (iv), the test drug applied in step ii) can be identified as a T-type α1H calcium channel inhibitor or at least a candidate for it.

In step iii), depolarization of the cells is induced by treating the cells with KCl or barium, where the concentration of KCl is preferably 10 mM~100 mM, out of which the most desirable range is 50 mM~60 mM.

FIG. 8 shows a protocol of a high throughput screening system using the cell line of the present invention. It is to be understood that this is just an example to which the scope and spirit of the present invention is not limited.

The present invention further provides a recombinant vector hKir2.1-pcDNA3.1(+) containing the gene represented by SEQ. ID. No 1, which encodes the human potassium channel.

The present inventors have cloned the DNA (hKir2.1 cDNA) of SEQ ID NO:1, encoding the human potassium channel by PCR with a pair of primers designed to have the sequences represented by SEQ ID NOS:3 and 4, using a template from a human brain cDNA library.

The cloned hKir2.1 cDNA was sub-cloned into BamHI and XhoI restriction enzyme sites of pcDNA3.1(+) vector (Invitrogen, USA) harboring the mammalian CMV promoter, so that the gene could be expressed stably in the mammalian cell line HEK293, resulting in the construction of hKir2.1-pcDNA3.1(+) vector. The cleavage map of the vector is presented in FIG. 3.

The recombinant vector of the present invention can contribute to the formation of intracellular resting membrane potential when inserted into the cells expressing T-type α1H calcium channel.

Practical and presently preferred embodiments of the present invention are illustrated as shown in the following Examples.

However, it will be appreciated that those skilled in the art, on consideration of this disclosure, may make modifications and improvements within the spirit and scope of the present invention.

Example 1

Cloning and Sub-Cloning of the Human Kir2.1 Potassium Channel

To amplify hKir2.1 gene specifically by PCR, the present inventors designed PCR primers as follows.

```
Forward primer:
5'ACTGGAGTCCCCAGCAGAA3';      (SEQ ID NO:3)

Reverse primer:
5'AGACCGTGTTGTAAAGTAACT3'     (SEQ ID NO:4)
```

As a template for the PCR, complementary DNA (cDNA) was synthesized by reverse transcription using AMV reverse transcriptase (Dakara, Japan) from 0.5 mg of human brain RNA library (Invitrogen, USA). PCR was performed using Taq DNA polymerase as follows; predenaturation at 94° C. for 1 minute, denaturation at 94° C. for 30 seconds, annealing at 52° C. for 30 seconds, polymerization at 72° C. for 1 minute and 20 seconds, 30 cycles from denaturation to polymerization. The resultant PCR product cDNA was separated in an 1% agarose gel and purified, and then cloned into TOPO TA vector (Invitrogen, USA). The PCR product obtained from the transformation was confirmed by sequencing, and as a result, the nucleotide sequence was identified as cDNA of human potassium channel Kir2.1. The nucleotide sequence (represented by SEQ ID NO:1) and the translated amino acid sequence (represented by SEQ ID NO:2) are shown in FIG. 1 and FIG. 2.

The cloned hKir2.1 cDNA was sub-cloned in the BamHI and XhoI sites of pcDNA3.1(+) vector (Invitrogen, USA) harboring a mammalian CMV promoter for the stable expression of hKir2.1 cDNA in the mammalian cell line HEK293 to bring about the construction of hKir2.1-pcDNA3.1(+) vector. The cleavage map of the vector is shown in FIG. 3.

Example 2

Culture of HEK293 Cell Line and Transfection with hKir2.1-pcDNA3.1(+) Vector Containing a Human Potassium Channel Gene Kir2.1

A HEK293 cell line with stably expressed human T-type α1H channels (Genebank accession No.: AF051946) has been established by Dr. Perez-Reyes (University of Virginia, USA), one of the inventors, and was used for the present invention. For the culture of the cell line, DMEM (Dulbecco's Modified Eagle's Medium, Sigma, USA) supplemented with 10% FBS (fetal bovine serum, GibcoBRL, USA), 2.5 g/L sodium bicarbonate, 100,000 unit/L penicillin, and 100 mg/L streptomycin (Life Technology, USA) was used. HEK293 cell line was sub-cultured in a 37° C. $CO_2$ incubator (humidified $CO_2$ incubator; 95% air-5% $CO_2$) at a 7-day interval. G-418, a geneticin-selective antibiotic, (Life Technology, USA) was additionally included in the medium. The medium was replaced with a fresh one every three days, to maintain the cell line expressing T-type α1H channel stably.

The calcium phosphate transfection kit (Invitrogen, USA) was used in the present invention to insert hKir2.1-pcDNA3.1 (+) vector, prepared in the above Example 1, into the HEK293 cell line stably expressing the human T-type α1H channel. Particularly, 24 hours before the transfection with the vector using calcium phosphate ($CaPO_4$), $2\times10^5$ cells were seeded on a 35 mm culture dish (Corning, USA) and the medium was replaced with a fresh one (the composition of the medium was the same as the above) 3-4 hours before the transfection. For the transfection, 7.5 μL of 2M $CaCl_2$ and 1 μg of hKir2.1-pcDNA3.1(+) vector were put in an E-tube (Eppendorf tube) and the volume of the tube was adjusted to 60 μL, followed by stirring. The vector solution was slowly dropped into the other tube containing 60 μL 2× Hank's buffered saline (HBS) for 1-2 minutes, accompanied by bubbling and stirring. When the vector precipitate was formed, it was left at room temperature for 30 minutes, and then was slowly allowed to fall onto the 35 mm culture dish pre-inoculated with the cells. The culture dish was smoothly shaken for an adequate mixing of the vector precipitate, which was then cultured in a $CO_2$ incubator for 24 hours. Upon completion of the culture after 24 hours, the medium was replaced with a fresh one.

Example 3

Selection of Transfected Cells and Culture of the Cell Clones

Cells were cultured in a medium containing G418 (1 mg/mL) and hygromycin (0.1 mg/mL) for 4 weeks after the transfection, followed by selection of a colony transformed by the stable expression of the T-type α1H channel hCav3.2 and potassium channel hKir2.1. The colonies survived from the antibiotics above were separated with a cloning cylinder, followed by a treatment with trypsin to obtain single cells. The single cells were inoculated into a 24-well plate, and further cultured to obtain 25 other cell clones.

Example 4

Confirmation of the Optimally Transformed Cell Line by Electrophysiological Methods The present inventors investigated the expression level of hKir2.1, current density of T-type α1H channels, resting membrane potential and cell homogeneity in 25 clones selected in Example 3, by using electrophysiological methods (current and voltage clamp techniques), and as a result, clone #30 was obtained, being the most suitable one for a HTS based on fluorescence calcium assays. The clone was deposited at the Korean Collection for Type Cultures (KCTC) of the Korea Research Institute of Bioscience and Biotechnology (KRIBB) on Feb. 22, 2005 (Accession No: KCTC 10780BP).

The procedures and conditions of the experiment were as follows. The T-type calcium current and inwardly rectifying potassium current (referred as "IRK current" hereinafter) were recorded by the whole-cell ruptured patch-clamp method (Hamil et al., *Pflugers Arch.*, 391:85-100, 198; Jeong and Ikeda, *Neuron*, 21:1201-1212, 1998), a voltage clamp technique, to confirm which clone could best express the human T-type α1H channel and human potassium channel Kir2.1. In the meantime, the resting membrane potential of the clones that were confirmed by the measurement of calcium and potassium currents was monitored by the gramicidin-perforated current-clamp method (Akaike, *Prog. Biophys. Mol. Biol.*, 65:251-264, 1997).

The patch electrode used in the measurement above was prepared with a borosilicate glass tube (Corning, USA) by a P-97 flaming brown micro-pipette puller (Sutter Instrument, USA). The electrode showed 1-3 MΩ of resistance when the internal solution was filled in. The cell capacitance and series resistance were adjusted to more than 80% by using Axopatch-1D (Axon Instruments, USA) or EPC-10 amplifier (HEKA, Germany). S4 (prepared by Dr. Stephen R. Ikeda, USA) using ITC18 (Instrutech, USA) or Pulse (HEKA, Germany) was used for the generation and data collection of the voltage-stimulating protocol. The ion current was low-pass filtered at 5 KHz by a 4-pole Bessel filter, and then digitized at 2 KHz. The results were recorded in a computer. The IGOR program (Wavemetrics, USA) was used to analyze the data. For the gramicidin-perforated current-clamp, the stock solution was prepared by dissolving gramicidin (Sigma, USA) in 50 μg/ml DMSO, which was later diluted to 50 μg/ml with internal solution before the measurement of voltage.

The compositions of the external and internal solutions used for the measurement of current and voltage are as follows.

① For Calcium Current:
Internal Solution (in mM)—
120 N-methyl-D-glucamine-methanesulfonate (NMG-MS), 20 tetraethyl-ammonium (TEA)-MS, 20 HCl, 11 EGTA, 1 $CaCl_2$, 10 HEPES, 4 Mg-ATP, 0.3 Na-GTP, 14 creatine phosphate (pH 7.4)
External Solution (in mM)—
155 Tris-AMEM, 20 HEPES, 10 $CaCl_2$, 10 glucose, 0.0003 tetrodotoxin (TTX) (pH 7.4)

② For Potassium Current:
Internal Solution (in mM)—
140 K+ gluconate, 5 NaCl, 1 EGTA, 2 $MgCl_2$, 10 HEPES, 2 Na-ATP, 0.1 Na-GTP (pH 7.3)
External Solution (in mM)—
135 NaCl, 5.4 KCl, 1 $MgCl_2$, 1.8 $CaCl_2$, 5 HEPES, 10 glucose (pH 7.4)

③ For Resting Membrane Potential:
Internal Solution (in mM)—
140 KCl, 5 EGTA, 10 HEPES, 0.5 $CaCl_2$, 5 NaCl (pH 7.2)
External Solution (in mM)—
135 NaCl, 5.4 KCl, 1 $MgCl_2$, 1.8 $CaCl_2$, 5 HEPES, 10 glucose (pH 7.4)

The results of the experiments performed hereinbefore are as follows.

Figure 4:
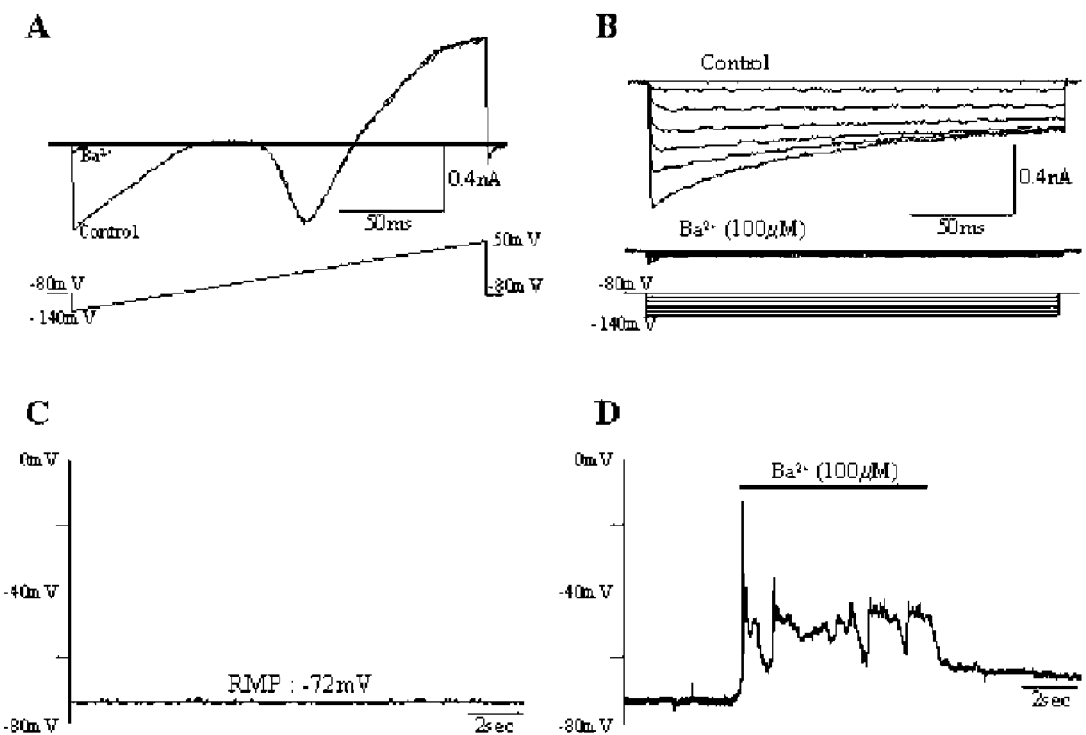
FIG. 4 is a set of graphs showing the result of electrophysiological compatibility test of HEK293-TChH-IRK2.1 cell line of the present invention.

As shown in FIG. 4A, the IRK current, generated from the potassium channel encoded by hKir2.1, and most activated at −140 mV was recorded where $_{2+}$ the applied ramp voltage to clone #30 varies from −140 mV to +50 mV with the voltage of clone #30 cells fixed at −80 mV. The T-type α1H channel current, activated at −50 mV and showing maximum activity at −30 mV, was recorded as well. The average current densities of IRK and T-type α1H channels were 24.9±5.7 pA/pF and 50±14.8 pA/pF (number of tests=3~6), respectively. The IRK current was blocked by 100 mM $Ba^{2+}$, a selective blocker (FIG. 2B). Such IRK current, sensitive to barium, was activated by a test pulse +10 mV increments starting from −140 mV. Whether or not a high resting membrane potential was generated when the expression of hKir2.1 was stably induced in the HEK293 cell line was investigated by a current clamp technique. In the procedure, the gramicidin-perforated patch-clamp was used to accurately measure the resting membrane potential without changing the composition of intracellular ions. The results shown in FIG. 2C confirmed that a high resting membrane potential of −72 mV was generated. The average resting membrane potential of control HEK293 cell line not expressing hKir2.1 (expressing T-type α1H channel, though) was −26.7±3.9 mV, which, by the stable expression of hKir2.1, could be increased up to −66.2±4.2 mV, a statistically significant number ($p<0.001$). When the resting membrane potentials are compared, the case of the cells expressing hKir2.1 stably was statistically higher ($p<0.05$) than those transiently expressing hKir2.1 (−57.6±4.8 mV). Meanwhile, the test results from other clones indicate that the generated resting membrane potential did not increase in proportion to the IRK current density detected in the HEK293 cells, but rather the over-expression of hKir2.1 reduced the current density of T-type α1H channels. As shown in FIG. 4D, 100 μM barium, an IRK inhibitor, was given to the cell while measuring the membrane potential of clone #30 by a current clamp method, $Ca^{2+}$ spikes or action potentials were induced with depolarization. The result suggests that in HEK293 cells without sodium channels, sufficient numbers of T-type α1H channels are activated by depolarization and calcium influx through the channel is abundant. This is due to the increase in the number of T-type α1H channels capable of activation when depolarized, which in turn owes to the high resting membrane potential generated by the stable expression of hKir2.1. Considering all the results from the electrophysiological tests, clone #30 was proved to be the most adequate for establishing a HTS system since the clone meets the necessary conditions of a high resting membrane potential while maintaining a high current density in T-type α1H channels.

Example 5

Investigation of the Compatibility of Cell Line (#30) by a Fluorescent Assay

Using the cell line (#30) confirmed by electrophysiological methods, a non-electrophysiological fluorescent calcium assay was employed to check whether or not (1) high calcium signals were detectable, and (2) the calcium signal could be blocked by non-specific T-type channel inhibitors.

Intracellular calcium concentrations were measured by the ratio fluorescence system (Ratiomaster, Photon Technology International, USA) installed on a fluorescent microscope (Nikon TE2000, Japan) as well as CoolSNAP CCD imaging system (Loafer Scientific, USA). Particularly, Fura-2/AM or Fluo-3 (Molecular Probes, USA) was added up to 5 μM to cells cultured on a cover slip, followed by loading at room temperature for 30-60 minutes with the light blocked. After the loading, the cells were washed twice with an extracellular flushing medium, and then the cover slip, on which the cells were stuck, was put on a perfusion chamber on the microscope. In the case of Fura-2/AM, the changes in the intracellular calcium ($Ca^{2+}$) concentration were measured using a photomultiplier (PM) tube in the ratio of fluorescence ($F_{340}/F_{380}$ t) emitted at 510 nm when 340 nm and 380 nm were used for excitation respectively. When Fluo-3 was used, fluorescent ratios were not measured but the fluorescent image emitted at 525 nm was recorded and captured by a cooled CCD, which was then analyzed by the Metaimage 6.1 program (Imaging Corporation, USA).

Whereas T-type α1H channels were activated by voltage stimulation in the patch clamp experiments, depolarization by adding barium or KCl outside the cells was essential in non-electrophysiological fluorescence measurements, since the cell itself had enough resting membrane potential. As shown in FIG. 5, depolarization was induced in a single cell of clone #30 (expressing T-type α1H channel and hKir2.1 stably) loaded with Fura-2/AM by adding 60 mM KCl, resulting in the increase of $F_{340}/F_{380}$ ratio from 1.1 to 1.55. The increase in intracellular calcium levels by the influx through T-type α1H channels, was completely inhibited by the pre-treatment of mibefradil (3 μM), a non-specific T-type channel inhibitor. As summarized in FIG. 6, the change in $F_{340}/F_{380}$ ratio according to the depolarization in clone #30 cells was 0.18±0.06 (number of tests=6) and 0.59±0.07 (number of tests=6), when the calcium concentration in the extracellular fluid was 2 mM and 10 mM respectively, meaning the ratio increased in proportion to the calcium concentration in the extracellular fluid.

Figure 7:
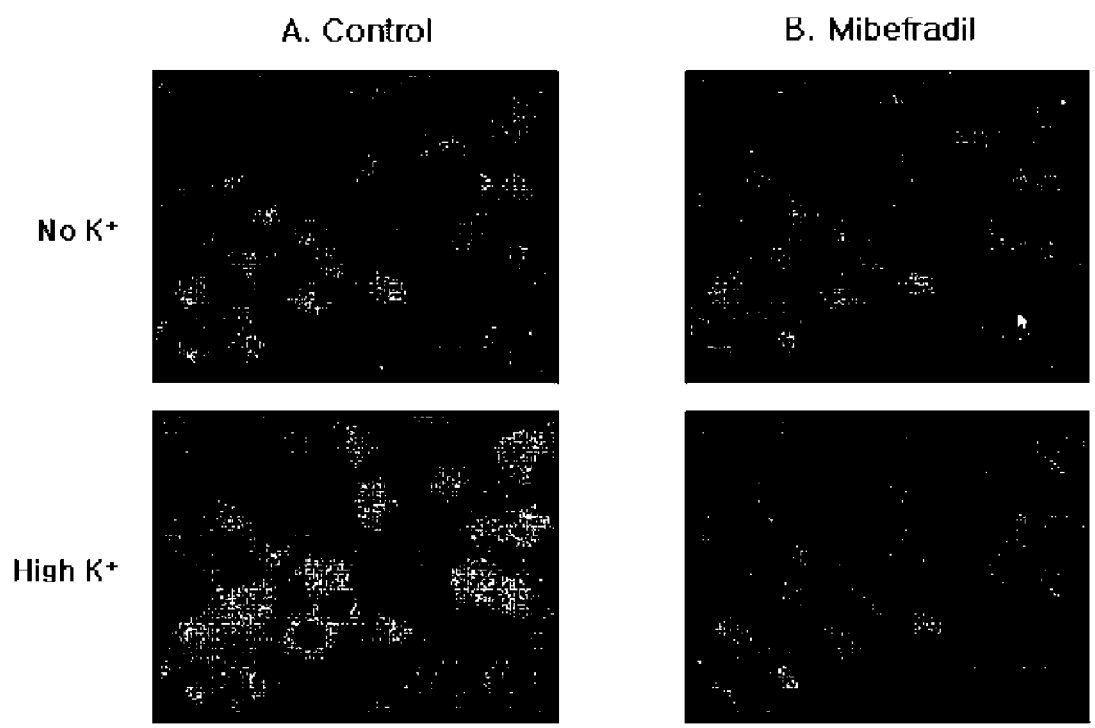
FIG. 7 is a set of photographs showing the results from the examination in the cell line HEK293-TChH-IRK2.1 of the present invention by a fluorescent calcium imaging experiment. The variations of the calcium signal in many cells were captured by a cooled CCD camera after loading Fluo-3 to the cells and were transformed into digital fluorescence image (the fluorescent calcium image generated by the addition of a high concentration of KCl was completely blocked by mibefradil, a non-specific T-type channel inhibitor).

The cooled CCD imaging system which can simultaneously measure fluorescent images of calcium signals from various cells, provides an experimental environment and principles similar to those provided by the fluorescent imaging plate reader (FLIPLR) used in a high throughput screening of drugs. Thus, the present inventors conducted the final confirmation by using the above imaging system whether or not the present invention was adequate for the detecting T-type α1H channel inhibitors by HTS. To measure fluorescent calcium image, Fluo-3 was loaded to clone #30 cells. The reason why Fluo-3 was used instead of Fura-2/AM in the calcium image measurement herein was that Fluo-3 has been known to be the fluorescent dye widely used in cell-based HTS studies for new drug development (Velicelebi et al., *Methods Enzymol.*, 294:20-47, 1999). FIG. 7 shows the fluorescent image of the intracellular calcium signal (red increased in proportion to the concentration of fluo-3 binding calcium). Even under a stable condition with no KCl, that is, non-depolarized state, the level of intracellular calcium was slightly elevated (some cells appeared red), which was reduced remarkably by mibefradil (3 μM), a non-specific T-type channel inhibitor, (the number of red cells were remarkably decreased). The above result indicates that some T-type α1H channels are activated even without a stimulus, under the stable resting membrane potential, so that a few calcium ions flows into the cell through T-type α1H channels (referred to as "window current"). However, it is not preferable to test drugs using this window current because of the low signal-to-noise ratio. When depolarization of clone #30 was induced by 60 mM KCl, the fluorescent image brightened very fast (FIG. 7A). Such increase in the intracellular calcium signal was completely inhibited by the pre-treatment of mibefradil (3 μM), a non-specific T-type channel inhibitor, (FIG. 7B) or 100 μM of nickel ($Ni^{2+}$).

INDUSTRIAL APPLICABILITY

The cell line of the present invention, which is capable of strong calcium signaling without external electrical stimuli, is suitable for a high throughput screening of T-type α1H calcium channel inhibitor candidates by the measurement of calcium fluorescence, and can further contribute to the development of therapeutic agents for a variety of diseases caused by the abnormal expression of T-type channels. In addition, broad spectrum studies on T-type α1H channels of their biophysical and pharmaceutical characteristics, gene expression, transport regulation, phosphorylation level and signal transduction, etc, that hitherto have been conducted in heterologous expression systems almost incapable of forming resting membrane potentials, can now be advanced in the cell line with a high resting membrane potential and excitability akin to neurons, bringing closer to elucidating the characteristics of T-type α1H channels and biological phenomena thereof.

What is claimed is:

1. A transfected cell line deposited under accession number KCTC 10780BP, which is prepared by introducing a recombinant vector comprising a polynucleotide encoding a potassium channel represented by SEQ ID NO:2 into a HEK293 cell line that stably expresses T-type α1H calcium channels.

2. The transfected cell line according to claim 1, wherein the polynucleotide encoding the potassium channel is human Kir2.1 gene represented by residues 1 to 1284 of SEQ ID NO:1.

3. The transfected cell line according to claim 1, wherein the cell line has a high resting membrane potential and its T-type α1H calcium channels can be activated by the treatment of potassium or barium salts.

4. A method of screening for T-type α1H calcium channel inhibitors comprising the following steps:

(i) loading a fluorescent dye into the cell line of claim 1;
(ii) adding a test drug into the cell line of the above step i);
(iii) depolarizing the cell line of the above step ii);
(iv) measuring the fluorescence intensity in the cell line of the above step iii); and
(v) identifying the test drug applied in step ii) as a T-type α1H calcium channel inhibitor by monitoring the cells showing no fluorescence changes or weak fluorescence in step (iv).

5. The method according to claim 4, wherein the depolarizing step iii) is accomplished by treating the cell line with potassium or barium salts.

6. The method according to claim 5, wherein the potassium salt is potassium chloride.

7. The method according to claim 6, wherein the concentration of potassium chloride is between 50 mM and 60 mM.

* * * * *

```
                        SEQUENCE LISTING

<160> NUMBER OF SEQ ID NOS: 4

<210> SEQ ID NO 1
<211> LENGTH: 1326
<212> TYPE: DNA
<213> ORGANISM: Homo sapiens

<400> SEQUENCE: 1
atgggcagtg tgcgaaccaa ccgctacagc atcgtctctt cagaagaaga cggtatgaag     60
ttggccacca tggcagttgc aaatggcttt gggaacggga agagtaaagt ccacaccga    120 caacagtgca ggagccgctt tgtgaagaaa gatggccact gtaatgttca gttcatcaat    180
gtgggtgaga aggggcaacg gtacctcgca gacatcttca ccacgtgtgt ggacattcgc    240
tggcggtgga tgctggttat cttctgcctg gctttcgtcc tgtcatggct gttttttggc    300
tgtgtgtttt ggttgatagc tctgctccat ggggacctgg atgcatccaa agagggcaaa    360
gcttgtgtgt ccgaggtcaa cagcttcacg gctgccttcc tcttctccat tgagacccag    420
acaaccatag gctatggttt cagatgtgtc acggatgaat gcccaattgc tgtttttcatg    480 gtggtgttcc agtcaatcgt gggctgcatc atcgatgctt catcattgg cgcagtcatg    540 gccaagatgg caaagccaaa gaagagaaac gagactcttg tcttcagtca caatgccgtg    600
attgccatga gagacggcaa gctgtgtttg atgtggcgag tgggcaatct tcggaaaagc    660
cacttggtgg aagctcatgt tcgagcacag ctcctcaaat ccagaattac ttctgaaggg    720
gagtatatcc ctctggatca aatagacatc aatgttgggt tgacagtgg aatcgatcgt    780 atatttctgg tgtccccaat cactatagtc catgaaatag atgaagacag tccttttatat    840 gatttgagta aacaggacat tgacaacgca gactttgaaa tcgtggtcat actggaaggc    900
atggtggaag ccactgccat gacgacacag tgccgtagct cttatctagc aaatgaaatc    960
ctgtggggcc accgctatga gcctgtgctc tttaagagaa agcactacta caaagtggac   1020
tattccaggt tccacaaaac ttacgaagtc cccaacactc ccctttgtag tgccagagac   1080
ttagcagaaa agaaatatat cctctcaaat gcaaattcat tttgctatga aatgaagtt   1140 gccctcacaa gcaaagagga agacgacagt gaaaatggag ttccagaaag cactagtacg   1200
gacacgcccc tgacataga ccttcacaac caggcaagtg tacctctaga gcccaggccc   1260
ttacggcgag agtcggagat atgagactga ttccttctct ggaatagtta ctttacaaca   1320
cggtct                                                              1326

<210> SEQ ID NO 2
<211> LENGTH: 427
<212> TYPE: PRT
<213> ORGANISM: Homo sapiens

<400> SEQUENCE: 2

Met Gly Ser Val Arg Thr Asn Arg Tyr Ser Ile Val Ser Ser Glu Glu
  1               5                  10                  15

Asp Gly Met Lys Leu Ala Thr Met Ala Val Ala Asn Gly Phe Gly Asn
             20                  25                  30

Gly Lys Ser Lys Val His Thr Arg Gln Gln Cys Arg Ser Arg Phe Val
```

-continued

```
                35                  40                  45
Lys Lys Asp Gly His Cys Asn Val Gln Phe Ile Asn Val Gly Glu Lys
         50                  55                  60

Gly Gln Arg Tyr Leu Ala Asp Ile Phe Thr Thr Cys Val Asp Ile Arg
 65                  70                  75                  80

Trp Arg Trp Met Leu Val Ile Phe Cys Leu Ala Phe Val Leu Ser Trp
                 85                  90                  95

Leu Phe Phe Gly Cys Val Phe Trp Leu Ile Ala Leu Leu His Gly Asp
            100                 105                 110

Leu Asp Ala Ser Lys Glu Gly Lys Ala Cys Val Ser Glu Val Asn Ser
        115                 120                 125

Phe Thr Ala Ala Phe Leu Phe Ser Ile Glu Thr Gln Thr Thr Ile Gly
    130                 135                 140

Tyr Gly Phe Arg Cys Val Thr Asp Glu Cys Pro Ile Ala Val Phe Met
145                 150                 155                 160

Val Val Phe Gln Ser Ile Val Gly Cys Ile Ile Asp Ala Phe Ile Ile
                165                 170                 175

Gly Ala Val Met Ala Lys Met Ala Lys Pro Lys Lys Arg Asn Glu Thr
            180                 185                 190

Leu Val Phe Ser His Asn Ala Val Ile Ala Met Arg Asp Gly Lys Leu
        195                 200                 205

Cys Leu Met Trp Arg Val Gly Asn Leu Arg Lys Ser His Leu Val Glu
    210                 215                 220

Ala His Val Arg Ala Gln Leu Leu Lys Ser Arg Ile Thr Ser Glu Gly
225                 230                 235                 240

Glu Tyr Ile Pro Leu Asp Gln Ile Asp Ile Asn Val Gly Phe Asp Ser
                245                 250                 255

Gly Ile Asp Arg Ile Phe Leu Val Ser Pro Ile Thr Ile Val His Glu
            260                 265                 270

Ile Asp Glu Asp Ser Pro Leu Tyr Asp Leu Ser Lys Gln Asp Ile Asp
        275                 280                 285

Asn Ala Asp Phe Glu Ile Val Val Ile Leu Glu Gly Met Val Glu Ala
    290                 295                 300

Thr Ala Met Thr Thr Gln Cys Arg Ser Ser Tyr Leu Ala Asn Glu Ile
305                 310                 315                 320

Leu Trp Gly His Arg Tyr Glu Pro Val Leu Phe Glu Glu Lys His Tyr
                325                 330                 335

Tyr Lys Val Asp Tyr Ser Arg Phe His Lys Thr Tyr Glu Val Pro Asn
            340                 345                 350

Thr Pro Leu Cys Ser Ala Arg Asp Leu Ala Glu Lys Lys Tyr Ile Leu
        355                 360                 365

Ser Asn Ala Asn Ser Phe Cys Tyr Glu Asn Glu Val Ala Leu Thr Ser
    370                 375                 380

Lys Glu Glu Asp Asp Ser Glu Asn Gly Val Pro Glu Ser Thr Ser Thr
385                 390                 395                 400

Asp Thr Pro Pro Asp Ile Asp Leu His Asn Gln Ala Ser Val Pro Leu
                405                 410                 415

Glu Pro Arg Pro Leu Arg Arg Glu Ser Glu Ile
            420                 425

<210> SEQ ID NO 3
<211> LENGTH: 19
<212> TYPE: DNA
<213> ORGANISM: Artificial Sequence
```

```
<220> FEATURE:
<223> OTHER INFORMATION: forward primer

<400> SEQUENCE: 3
actggagtcc ccagcagaa                                              19

<210> SEQ ID NO 4
<211> LENGTH: 21
<212> TYPE: DNA
<213> ORGANISM: Artificial Sequence
<220> FEATURE:
<223> OTHER INFORMATION: reverse primer

<400> SEQUENCE: 4
agaccgtgtt gtaaagtaac t                                           21
```